US009182271B2

(12) United States Patent
Grigoriev et al.

(10) Patent No.: US 9,182,271 B2
(45) Date of Patent: Nov. 10, 2015

(54) METHODS OF MEASURING A CHARACTERISTIC OF A CREPING ADHESIVE FILM AND METHODS OF MODIFYING THE CREPING ADHESIVE FILM

(71) Applicant: Kemira Oyj, Helsinki (FI)

(72) Inventors: Vladimir Grigoriev, Atlanta, GA (US); Danny Nguyen, Norcross, GA (US); Scott Rosencrance, Douglasville, GA (US); Chen Lu, Marietta, GA (US)

(73) Assignee: KEMIRA OYJ, Helsinki (FI)

( * ) Notice: Subject to any disclaimer, the term of this patent is extended or adjusted under 35 U.S.C. 154(b) by 0 days.

(21) Appl. No.: 14/575,216

(22) Filed: Dec. 18, 2014

(65) Prior Publication Data

US 2015/0101410 A1  Apr. 16, 2015

Related U.S. Application Data

(62) Division of application No. 13/804,005, filed on Mar. 14, 2013.

(60) Provisional application No. 61/612,645, filed on Mar. 19, 2012.

(51) Int. Cl.
*G01H 13/00* (2006.01)
*G01N 29/036* (2006.01)

(52) U.S. Cl.
CPC .............. *G01H 13/00* (2013.01); *G01N 29/036* (2013.01); *G01N 2291/0237* (2013.01); *G01N 2291/0426* (2013.01)

(58) Field of Classification Search
CPC . G01N 29/022; G01N 29/036; G01N 33/343; G01N 2291/0426; G01N 2291/0256; G01N 2291/0258; G01N 2291/0241; G01N 2291/02416; G01N 2291/0228; G01H 13/00; D21H 21/146
See application file for complete search history.

(56) References Cited

U.S. PATENT DOCUMENTS

| | | | |
|---|---|---|---|
| 5,201,215 | A | 4/1993 | Granstaff et al. |
| 5,734,098 | A | 3/1998 | Kraus et al. |
| 5,869,763 | A | 2/1999 | Vig et al. |
| 6,247,354 | B1 | 6/2001 | Vig et al. |
| 6,649,208 | B2 | 11/2003 | Rodgers |
| 6,651,488 | B2 | 11/2003 | Larson |
| 7,036,375 | B2 | 5/2006 | Nozaki |
| 7,585,388 | B2 | 9/2009 | Yeh et al. |
| 7,842,165 | B2 | 11/2010 | Shevchenko et al. |
| 8,160,305 | B2 * | 4/2012 | Laurint et al. ................. 382/111 |
| 8,182,861 | B2 | 5/2012 | Lee et al. |
| 8,500,957 | B2 * | 8/2013 | Shevchenko et al. ......... 162/198 |
| 8,551,292 | B2 * | 10/2013 | Goto et al. .................... 162/198 |
| 8,945,371 | B2 * | 2/2015 | Kouznetsov et al. ...... 205/793.5 |
| 2004/0187580 | A1 | 9/2004 | Nozaki |
| 2006/0144335 | A1 | 7/2006 | Lee et al. |
| 2006/0232281 | A1 | 10/2006 | Vittorio et al. |
| 2006/0281191 | A1 | 12/2006 | Duggirala et al. |
| 2008/0163688 | A1 | 7/2008 | Wang et al. |
| 2009/0056897 | A1 | 3/2009 | Shevchenko et al. |
| 2011/0027459 | A1 | 2/2011 | Lee et al. |
| 2011/0061462 | A1 | 3/2011 | Ichihashi et al. |
| 2011/0073263 | A1 | 3/2011 | Shevchenko et al. |
| 2011/0085759 | A1 | 4/2011 | Lee et al. |
| 2011/0122410 | A1 | 5/2011 | Wang et al. |
| 2011/0309821 | A1 | 12/2011 | Kondo et al. |
| 2012/0073775 | A1 | 3/2012 | Duggirala et al. |
| 2012/0078541 | A1 | 3/2012 | Hesketh et al. |
| 2012/0211190 | A1 | 8/2012 | Goto et al. |
| 2013/0245158 | A1 | 9/2013 | Grigoriev et al. |
| 2014/0053779 | A1 | 2/2014 | Martinson et al. |
| 2014/0110071 | A1 * | 4/2014 | Furman et al. ................. 162/111 |

OTHER PUBLICATIONS

International Search Report and Written Opinion dated Aug. 8, 2013.

* cited by examiner

*Primary Examiner* — Jose Fortuna
(74) *Attorney, Agent, or Firm* — Thomas Horstemeyer, LLP

(57) ABSTRACT

Described herein are quartz crystal microbalance (QCM) and quartz crystal microbalance with dissipation (QCMD) techniques that can be used for measuring characteristics of a creping adhesive film similar to the creping adhesive film that is formed on a Yankee dryer during the tissue and towel manufacturing process. In addition, exemplary embodiments described herein may use these techniques to predict performance of creping aids utilized to form a creping adhesive film.

20 Claims, 6 Drawing Sheets

METHODS OF MEASURING A CHARACTERISTIC OF A CREPING ADHESIVE FILM AND METHODS OF MODIFYING THE CREPING ADHESIVE FILM

CROSS-REFERENCE TO RELATED APPLICATION

This application is a divisional of and claims priority to U.S. Non-provisional application entitled "METHODS OF MEASURING A CHARACTERISTIC OF A CREPING ADHESIVE FILM AND METHODS OF MODIFYING THE CREPING ADHESIVE FILM," having Ser. No. 13/804,005, filed on Mar. 14, 2013, now abandoned which claims priority to provisional application entitled "METHODS OF MEASURING A CHARACTERISTIC OF A CREPING ADHESIVE FILM AND METHODS OF MODIFYING THE CREPING ADHESIVE FILM", having Ser. No. 61/612,645, filed on Mar. 19, 2012, which is entirely incorporated herein by reference.

BACKGROUND

1. Field of the Art

The present embodiments relate to measuring creping adhesive film characteristics.

2. Description of Related Art

A conventional creping process generally includes scraping a dried paper web from a drying cylinder (e.g., a Yankee dryer), such as by the use of a creping doctor blade. The creping action puts very small folds or accordions in the sheet which impart a fine, rippled texture to the sheet, which can increase the bulk, softness and absorbency of the sheet.

Adhesion of the sheet to the drying cylinder is one factor that contributes to how the sheet crepes at the doctor blade. Sheet adhesion may be controlled through application of an adhesive formulation onto the Yankee dryer surface. The creping process typically involves applying the creping adhesive, such as in the form of an aqueous solution or dispersion, to a drying surface for the web. Typically, this surface is the surface of a rotating heated creping cylinder, such as the Yankee dryer. The paper web is then adhered to the indicated surface and later dislodged from the surface with a creping device, e.g., a doctor blade. The impact of the web against the creping device ruptures some of the fiber-to-fiber bonds within the web, causing the web to wrinkle or pucker. In this regard, fibrous webs, particularly paper webs, are conventionally subjected to the creping process in order to give them desirable textual characteristics, such as softness and bulk. Adhesive formulations can improve product quality and control of the papermaking process.

Drying cylinders such as the Yankee dryer are often operated at a variety of temperature conditions, for example, ranging from about 90° C. to 130° C. Recent trends have the creping conditions moving towards high temperature and/or low sheet moisture. Under high temperature conditions, "rewettability" of the applied adhesive may affect adhesion of the sheet to the Yankee dryer. Rewettability refers to the ability of a dry adhesive film on the dryer to absorb water, e.g., once in contact with the wet paper sheet. The adhesive is typically sprayed on the Yankee coating continuously. However, the majority of the adhesion occurs by means of the adhesive deposited in previous passes. If the adhesive absorbs greater amounts of water in contact with the sheet, the adhesive will be softer, resulting in a more intimate contact with the sheet and providing increased adhesion between the sheet and the dryer.

The solubility of the adhesive film in water is another property affecting adhesion. The wet sheet before the Yankee dryer typically contains 60% or more water. During the contact between the wet sheet and the Yankee dryer, water from the sheet may wash off a portion of the deposited adhesive coating, which can decrease the efficiency of the creping process. It is often desirable to use an adhesive with low water solubility (high insolubility) so that the adhesive film can withstand wash-off at the point of contact with the wet sheet, and form a more durable coating on the Yankee surface.

Predicting performance of creping adhesives on a commercial machine is a challenging task, in part because of the extremely dynamic nature of the creping process. The primary indicator of performance of creping adhesives has been an adhesion test. The peel adhesion test is a common laboratory technique for characterizing adhesion of creping adhesives.

Adhesion is a complex phenomenon that can be affected by various parameters. In a common process, the adhesion development starts in the pressure roll nip at the point of the sheet transfer from the carrying fabric or felt onto the Yankee dryer cylinder. The moisture from the wet sheet can rewet the partially or completely dried adhesive coating, making it soft and pliable enough to form a good contact with the sheet but ideally not too soft that it is washed off the Yankee dryer surface. Water is an effective plasticizer of the creping adhesive film, and can affect the adhesive film softness. The rewet phenomenon affects the adhesion development. At the same time water can solubilize the adhesive film, and potentially render it useless and inefficient. A certain level of insolubility is desirable for the adhesion development. Therefore, characterization of film solubility, rewetting and softness characteristics can help develop an understanding of the adhesion development on the Yankee dryer and for predicting performance of creping adhesives.

Conventional methods for characterizing rewetting, solubility and softness characteristics of creping adhesive films involve preparation of uniform adhesive films, typically of a few millimeters in thickness. For rewetting and solubility measurements, the films are immersed into water under controlled agitation, temperature and time. The mass gain and/or loss of the films are then calculated to determine the rewet ratio or percent insolubility. For film softness measurements, films are tested using a durometer to determine a relative hardness or using a more sophisticated rheometer. In rheological measurements, the film undergoes mechanical stress under controlled temperature and stress rate. The film's resistance to stress is measured to yield shear modulus, for example, which can be used to characterize the film softness. The test time for many of these characterizations is greater than 10 hours, some test times are longer than 40 hours. Thus, it is difficult to use these tests to make real time adjustments. In addition, these methods require a preparation of thick films (a few millimeter thickness); whereas, in comparison the thickness of typical adhesive films on the Yanke dryer are about a few micrometers. The wetting and solubilization phenomena often depend on the thickness of the film and therefore the correlation of results of conventional test methods to process conditions may be relatively poor. Another potential downside of the conventional rewet methods is their use is often limited to insoluble or only partially soluble adhesive films—for fully-soluble adhesive films, moisture absorption may compete with the solubilization process, resulting in a mass loss measurements rather than a mass gain, typically sought from a rewet measurement.

The description herein of certain advantages and disadvantages of known methods and compositions is not intended to limit the scope of the present disclosure. Indeed the present embodiments may include some or all of the features described above without suffering from the same disadvantages.

SUMMARY

In view of the foregoing, one or more embodiments include methods of measuring a characteristic of a creping adhesive film, methods of modifying the creping adhesive film, and the like At least one embodiment provides a method of measuring a characteristic of a creping adhesive film, including disposing a creping adhesive film on a sensor substrate, measuring an oscillation frequency of the sensor substrate having the creping adhesive film disposed thereon using a Quartz Crystal Microbalance (QCM) technique, and determining a characteristic of the creping adhesive film.

At least one embodiment provides a method for modifying the creping adhesive film disposed on a Yankee dryer, including obtaining a sensor substrate having a creping adhesive film disposed thereon, where the creping adhesive film has a composition that is the same as a creping adhesive film disposed on a Yankee dryer, measuring an oscillation frequency of the sensor substrate having the creping adhesive film disposed thereon using a Quartz Crystal Microbalance (QCM) technique, determining a characteristic of the creping adhesive film, and modifying a composition of the creping adhesive film disposed on the Yankee dryer based on the determination of the characteristic.

DETAILED DESCRIPTION OF THE EMBODIMENTS

Figure 1A:
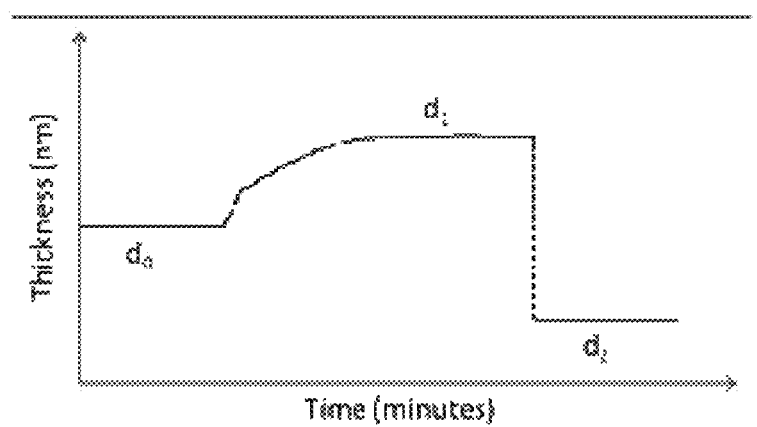
FIGS. 1A and 1B graphically illustrate film thickness profiles calculated from the QCMD test with a flow module.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic organic chemistry, paper chemistry, and the like, which are within the skill of the art. Such techniques are explained fully in the literature.

The examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms and phrases that shall be defined to have the following meanings unless a contrary intention is apparent.

DEFINITIONS

As used herein, the terms "paper" or "paper product" (these two terms can be used interchangeably herein) are understood to include a sheet material that contains paper fibers, which may also contain other materials. Suitable paper fibers include natural and synthetic fibers, for example, cellulosic fibers, wood fibers of all varieties used in papermaking, other plant fibers, such as cotton fibers, fibers derived from recycled paper; and the synthetic fibers, such as rayon, nylon, fiberglass, or polyolefin fibers. The paper product may be composed only of synthetic fibers. Natural fibers may be mixed with synthetic fibers. For instance, in the preparation of the paper product, the paper web, or paper material may be reinforced with synthetic fibers, such as nylon or fiberglass, or impregnated with nonfibrous materials, such as plastics, polymers, resins, or lotions. As used herein, the terms "paper web" and "web" are understood to include both forming and formed paper sheet materials, papers, and paper materials containing paper fibers. The paper product may be a coated, laminated, or composite paper material. The paper product can be bleached or unbleached.

Paper can include, but is not limited to, writing papers and printing papers (e.g., uncoated mechanical, total coated paper, coated free sheet, coated mechanical, uncoated free sheet, and the like), industrial papers, tissue papers of all varieties, paperboards, cardboards, packaging papers (e.g., unbleached kraft paper, bleached kraft paper), wrapping papers, paper adhesive tapes, paper bags, paper cloths, toweling, wallpapers, carpet backings, paper filters, paper mats, decorative papers, disposable linens and garments, and the like.

Paper can include tissue paper products. Tissue paper products include sanitary tissues, household tissues, industrial tissues, facial tissues, cosmetic tissues, soft tissues, absorbent tissues, medicated tissues, toilet papers, paper towels, paper napkins, paper cloths, paper linens, and the like. Common paper products include printing grade (e.g., newsprint, catalog, rotogravure, publication, banknote, document, bible, bond, ledger, stationery), industrial grade (e.g., bag, linerboard, corrugating medium, construction paper, greaseproof, glassine), and tissue grade (sanitary, toweling, condenser, wrapping).

In an exemplary embodiment, tissue paper may be a felt pressed tissue paper, a pattern densified tissue paper, or a high bulk, uncompacted tissue paper. In an exemplary embodiment, the tissue paper may be creped or uncreped, of a homogeneous or multilayered construction, layered or non-layered (blended), and one-ply, two-ply, or three or more plies. In an exemplary embodiment, tissue paper includes soft and absorbent paper tissue products that are consumer tissue products.

"Paperboard" is a paper that is thicker, heavier, and less flexible than conventional paper. Many hardwood and softwood tree species are used to produce paper pulp by mechanical and chemical processes that separate the fibers from the wood matrix. Paperboard can include, but is not limited to, semi-chemical paperboard, linerboards, containerboards, corrugated medium, folding boxboard, and cartonboards.

In an exemplary embodiment, paper refers to a paper product such as dry paper board, fine paper, towel, tissue, and newsprint products. Dry paper board applications include liner, corrugated medium, bleached, and unbleached dry paper board.

In an embodiment, paper can include carton board, container board, and special board/paper. Paper can include boxboard, folding boxboard, unbleached kraft board, recycled board, food packaging board, white lined chipboard, solid bleached board, solid unbleached board, liquid paper board, linerboard, corrugated board, core board, wallpaper base, plaster board, book bindery board, woodpulp board, sack board, coated board, gypsum board and the like.

"Pulp" refers to a fibrous cellulosic material. Suitable fibers for the production of the pulps are all conventional grades, for example mechanical pulp, bleached and unbleached chemical pulp, recycled pulp, and paper stocks obtained from all annuals. Mechanical pulp includes, for example, groundwood, thermomechanical pulp (TMP), chemothermochemical pulp (CTMP), groundwood pulp produced by pressurized grinding, semi-chemical pulp, high-yield chemical pulp and refiner mechanical pulp (RMP). Examples of suitable chemical pulps are sulfate, sulfite, and soda pulps. The unbleached chemical pulps, which are also referred to as unbleached kraft pulp, can be particularly used.

"Pulp slurry" refers to a mixture of pulp and water. The pulp slurry is prepared in practice using water, which can be partially or completely recycled from the paper machine. It can be either treated or untreated white water or a mixture of such water qualities. The pulp slurry may contain interfering substances (e.g., fillers). The filler content of paper may be up to about 40% by weight. Suitable fillers are, for example, clay, kaolin, natural and precipitated chalk, titanium dioxide, talc, calcium sulfate, barium sulfate, alumina, satin white or mixtures of the stated fillers.

"Papermaking process" is a method of making paper products from pulp comprising, inter alia, forming an aqueous pulp slurry that can include a cellulosic fiber, draining the pulp slurry to form a sheet, and drying the sheet. The steps of forming the papermaking furnish, draining, and drying may be carried out in any conventional manner generally known to those skilled in the art.

General Discussion

In various exemplary embodiments described herein, quartz crystal microbalance (QCM) and quartz crystal microbalance with dissipation (QCMD) techniques can be used for measuring characteristics of a creping adhesive film similar to the creping adhesive film that is formed on a Yankee dryer during the tissue and towel manufacturing process. In addition, exemplary embodiments discussed herein may use these techniques to predict performance of creping aids utilized to form a creping adhesive film. Furthermore, exemplary embodiments of the present disclosure can predict performance of creping aids utilized to form a creping adhesive film based on conditions (e.g. temperature, humidity, and the like) present in tissue and towel manufacturing processes. Additionally, exemplary embodiments described herein can be used to modify one or more characteristics of the creping adhesive film in real time to enhance and improve the tissue and towel manufacturing process.

The Quartz Crystal Microbalance (QCM) is a mass sensing device with the ability to measure very small mass changes on a quartz crystal resonator in real-time. The sensitivity of the QCM is approximately 100 times higher than an electronic fine balance with a sensitivity of 0.1 mg. This means that QCM's are capable of measuring mass changes as small as a fraction of a monolayer or single layer of molecules. QCM uses a voltage being applied to a quartz crystal causing it to oscillate at a specific frequency, where different voltages correspond to different frequencies. Changes in mass on the quartz surface are related to changes in frequency of the oscillating crystal through the Sauerbrey relationship. Further theory and practical aspects of QCM can be found in *Applications of Piezoelectric Quartz Crystal Microbalances*; C. Lu, A. W. Czanderna, ed., Amsterdam: Elsevier 1984, which is incorporated herein by reference.

The Sauerbrey relation is valid for rigid, evenly distributed, and sufficiently thin adsorbed layers (e.g., dry creping adhesive film). However, for soft or viscoelastic films (e.g., wet creping adhesive film) that do not fully couple to the oscillating crystal, the Sauerbrey relationship may underestimate the mass.

For viscoelastic films, Quartz Crystal Microbalance with Dissipation (QCMD) may be more appropriate. QCMD measures both frequency and dissipation of the quartz crystal. Dissipation occurs when the driving voltage to the crystal is shut off and the energy from the oscillating crystal dissipates from the system. The frequency of the oscillating quartz crystal changes with the mass on the sensor. When molecules adsorb to an oscillating quartz crystal, water (or other liquid) couples to the adsorbed material (e.g., the creping adhesive layer) as an additional dynamic mass via direct hydration and/or entrapment within the adsorbed film. Thus, the layer is sensed as a viscoelastic "hydrogel" composed of the molecules and the coupled water. By measuring the dissipation, one can determine if the adsorbed film is rigid or viscoelastic (soft), which is not possible looking only at the frequency response.

Dissipation measurements enable qualitative analysis of the structural properties of adsorbed molecular layers. Different materials can easily be compared and one can ascertain if the Sauerbrey relation will accurately approximate the adsorbed mass or not. Furthermore, the QCMD technology allows quantitative analysis of the mass, thickness, viscosity and complex shear modulus, for example, of the adsorbed films (e.g., the creping adhesive layer) whereas these measurements are well beyond the Sauerbrey regime. This is achieved by combining frequency and dissipation measurements from multiple harmonics (overtones) and applying simulations using a Voigt-based viscoelastic model. QCMD enables real-time measurements of both mass and structural properties of molecular layers. Measuring the dissipation parameter allows accurate analysis of soft films that do not obey the linear relation between change in frequency and change in mass. A basic explanation of the QCMD technology is found in *Energy Dissipation Kinetics for Protein and Antibody-Antigen Adsorption under Shear Oscillation on a Quartz Crystal Microbalance* in Langmuir 1998, 14, 729-734 by Hook et al, which is incorporated herein by reference. Interpretation of QCMD data and applying the viscoelastic model is well described in: *Analysis of Interpenetrating Polymer Networks via Quartz Crystal Microbalance with Dissipation monitoring* in Langmuir. 2005 Jun. 7; 21(12):5529-36 by Irwin et al, which is incorporated herein by reference.

In an exemplary embodiment, QCM and/or QCMD techniques can be used to characterize one or more properties of a creping adhesive film. Creping adhesive films tend to be rigid when they are completely dry but when the films absorb moisture they become soft (viscoelastic). QCM, QCMD, or a combination of thereof can provide valuable information on the interaction of moisture with the adhesive films and their viscoelastic characteristics. In an exemplary embodiment, QCM techniques can be used to measure rigid films and QCMD techniques can be used to measure soft films. This information can be used to modify one or more components or properties of the creping adhesive films, the temperature of the environment around the creping adhesive films, the humidity of the environment around the creping adhesive films, or the like, or a combination thereof.

In an exemplary embodiment, the creping adhesive film can be disposed (e.g., cast) on a quartz crystal sensor using any of various known or later-developed techniques. Exemplary film deposition techniques include, for example, dip coating, sputtering, thermal evaporation, spin coating, and/or other appropriate method. In an exemplary embodiment, the creping adhesive film can have a thickness of about 1 nanometer to 1000 micrometers, which is consistent with the creping adhesive film thickness on a Yankee dryer. In an exemplary embodiment, the length and/or width of the creping adhesive film can vary depending on the dimensions of the sensor.

In general, quartz crystal sensors used in QCM and QCMD techniques are well known in the art. In an exemplary embodiment, the quartz crystal sensor can have a diameter of about 14 mm and a thickness of about 0.3 mm. In an exemplary embodiment, the sensor can have a metal, metal oxide layer, and/or polymer layer disposed on portions of and/or around the sensor. In an exemplary embodiment, the metal oxide can include: $SiO_2$, $Al_2O_3$, Ti, Pt, Ag, W, Cu, Cr, Ir, Ta, $FeC_3$, TaN, $CeO_2$, Fe, Zn, $ZnO_2$, $FeO_3$, ZnS, FeS, stainless steel, and the like. In an exemplary embodiment, the polymer can include PS, PC, PMMA, a fluoropolymer, PE, PP, and the like. In addition, the quartz crystal sensor includes appropriate contacts to connect with a device to drive and control the frequency and to measure the oscillation frequency change. The oscillation frequency data can be communicated to a device such as a computer, where the data can be subsequently analyzed and various characteristics determined about the creping adhesive film.

In an exemplary embodiment, the creping adhesive film can be cast on a quartz crystal using a spin coating technique. In an embodiment, the spin coating technique can be used to form a thickness of about a few nanometers or less of the creping adhesive film on the sensor. In an embodiment, these ultrathin films can be prepared within minutes, significantly accelerating the film preparation process compared to conventional methods described above.

After curing at a high temperature (e.g., about 50 to 150° C.) for a period of time (e.g., for about 60 min, about 30 min, or less), the creping adhesive film can be analyzed using a QCM and/or QCMD at one or more frequencies. In addition, the creping adhesive film can be exposed either to a water flow (also referred to as the flow module in the Example) or humid air (also referred to as the humidity module in the Example) in a QCM and/or QCMD chamber and changes in oscillation frequency can be recorded at one or more frequencies. The frequency data can be further analyzed using established models. In an exemplary embodiment, the frequency data can be used to generate one or more characteristics of the creping adhesive film (e.g., weight change, percent solubility, rewet ratio, film viscosity, film elasticity, shear modulus, percent insolubility, swelling ratio, film softness, film rigidity, and a combination thereof can be calculated), each of which can be analyzed as a function of moisture exposure (e.g., flow module and/or humidity module), temperature (e.g., about 10 to 100° C.), water flow rate, relative humidity (e.g., about 0 to 100%), film preparation conditions (cure time, cure temperature, film thickness, etc.), and a combination thereof. The variables of temperature and/or water exposure can be designed to resemble the actual conditions that the crepe adhesive film is experiencing during paper processing so modifications can be made in real time if desired. In an embodiment, film solubility, rewet ratio, weight change, and/or shear modulus of creping adhesive films can be measured separately or simultaneously depending on the crepe adhesive type and the instrument configuration. In an embodiment, the data and characteristics can be used to predict adhesive performance and can be used to modify, in real time, the composition of the components in the creping adhesive layer to improve the characteristics of the creping adhesive layer.

In an exemplary embodiment, the method of measuring a characteristic of a creping adhesive film includes disposing a creping adhesive film on a sensor substrate using one of the techniques described herein. One or more frequencies can be applied to the sensor substrate and the oscillation frequency of the sensor substrate can be measured using a QCM and/or QCMD technique. The data acquired can be used to determine one or more characteristics of the creping adhesive film. In an embodiment, one or more frequencies can be applied using the QCM and/or QCMD techniques to the sensor substrate under various conditions (e.g., modification of the temperature, exposure to humidity (before and after), exposure to water (before and after), and the like), where the conditions can be designed to resemble the actual processing conditions that the creping adhesion film is experiencing during tissue and towel production.

The exemplary embodiments may be used to characterize any creping adhesive. In an embodiment, the creping adhesive film can be made using one or more of the following components: a creping adhesive, a release aid, a modifier, a plasticizer, a humectant, a phosphate, a creping additive, a mineral, hemicellulose, a fiber, a fine, a fiber fragment, a softener, a debonder, a defoamer, wet strength resin, a dry strength resin, a charge control agent, a retention aid, a biocide, a dye, and a combination thereof. In an embodiment, the creping adhesive can include a polyvinyl alcohol, polyamine/epihalohydrin resin (e.g., PAE), polyacrylamide, carboxymethylcellulose, polyvinyl acetate, and the like. Components to make a creping adhesive film are known in the art. Embodiments of the present disclosure are not limited by the components of the creping adhesive film.

An exemplary embodiment of the present disclosure allows for the measurement of characteristics of the creping adhesive film as a function of one or more of the components that are used to make the creping adhesive film and/or that may become in contact (e.g., fibers, chemicals from the pulp slurry, and the like), and possible part of, the creping adhesive film. In addition, an exemplary embodiment of the present disclosure provides one of skill in the art information about the characteristics of the creping adhesive film so that the amounts and/or types of components of the creping adhesive film can be modified to achieve desired results. In an exemplary embodiment, the modification can occur in real time (e.g., less than about 1 hour) or near real time (e.g., about 1 to 8 hours or about 1 to 4 hours) unlike other methods. In an exemplary embodiment, the modification can be made prior to being implemented in the manufacturing process and measured using the QCM and/or QCMD technique to ensure that the desired characteristics are realized using the modified creping adhesive film. Thus, an exemplary embodiment of the present disclosure enables the creping adhesive film to be designed and tested prior to implementation.

As mentioned above, an exemplary embodiment of the present disclosure includes a method for modifying the creping adhesive film disposed on a Yankee dryer (e.g., in real time or near real time). In an exemplary embodiment, the method includes obtaining a sensor substrate having a creping adhesive film disposed thereon. In an embodiment, the creping adhesive film has a composition that is the same or similar to a creping adhesive film disposed on a Yankee dryer. Next, one or more frequencies can be applied to the sensor substrate and the oscillation frequency of the sensor substrate can be measured using a QCM and/or QCMD technique. The data acquired can be used to determine one or more characteristics of the creping adhesive film. In an embodiment, one or more frequencies can be applied using the QCM and/or QCMD techniques to the sensor substrate under various conditions (e.g., modification of the temperature, exposure to humidity (before and after), exposure to water (before and after), and the like), where the conditions can be designed to resemble the actual processing conditions that the creping adhesion film is experiencing. Once the data has been analyzed, the composition of the creping adhesive film disposed on the Yankee dryer can be modified (e.g., as described herein) based on the analysis of the characteristic(s) of the creping adhesive film. This process can be repeated as needed to obtain the desired creping adhesive film and resulting tissue or towel product. As noted above, the analysis may include modifying the composition of the creping adhesion film and testing it prior to implementing the modified creping adhesion film in the manufacturing process. Thus, an exemplary embodiment of the present disclosure enables the creping adhesive film to be designed and tested prior to implementation, which can be conducted in real time or near real time.

EXAMPLES

Now having described the embodiments, in general, the examples describe some additional embodiments. While embodiments are described in connection with the examples and the corresponding text and figures, there is no intent to limit embodiments of the disclosure to these descriptions. On the contrary, the intent is to cover all alternatives, modifications, and equivalents included within the spirit and scope of exemplary embodiments.

EXAMPLES

Experimental Data

Creping Adhesives:
Commercial polyamidoamine-epichlorohydrin resins were used in these studies, designated as Sample A, Sample B.

Conventional Tests:
Film insolubility and rewettability were measured in a combined test. For each adhesive sample, an adhesive film of a fixed thickness was prepared in a beaker by drying at 90° C. for 1 hr followed by 4 hr drying at 110° C. The dry film was weighed (initial dry film weight), covered with distilled water and agitated in a shaker at room temperature. The undissolved solids were separated, weighed (wet film weight after agitation in water), dried and weighed again (dry film weight after solubilization). The Percent Insolubility and Rewet Ratio were calculated as follows:

Percent Insolubility=[(Dry film weight after solubilization)/(Initial dry film weight)]×100

Rewet Ratio=(Wet film weight after agitation in water)/(Dry film weight after solubilization)

Film shear modulus was measured using an Anton Paar MCR 300 Rheometer. Adhesive films (1 mm thickness) were cast by drying at 90° C. for 5-8 hrs. Small disks having 8-mm in diameter were punched out of the adhesive films using a die. The disks were re-dried at 90° C. prior to testing. The geometry used for the oscillation test was parallel plates. The shear storage and the shear loss modulus were determined at 110° C., 100 Hz and 1% strain. The complex shear modulus referred to as "shear modulus" was calculated from the shear storage and shear loss moduli.

QCMD Test:
A creping adhesive solution was spin coated on a gold coated quartz crystal sensor. The adhesive coated sensors was dried and cured in an oven at 110° C. for 15 min. Depending on the adhesive solution and its viscosity, the film thickness of dry films ranged from about 20-150 nm.

A Q-Sense E4 system (Biolin Scientific AB, Västra Frölunda, Sweden) was used to make QCMD measurements for real-time studies of mass or thickness changes and viscoelastic properties of creping adhesive films exposed to moisture. Two QCMD modules were used. A flow module was used for measuring the film insolubility and rewet ratio parameters. In this module, water flows over the creping adhesive film. A humidity module was used for measuring the rewet ratio and shear modulus. In the humidity module, creping adhesive films were exposed to a controlled level of humid air. Relative humidity levels were generated by using various salt solutions that pass through a cell separated by a gas permeable membrane. The membrane prevented the coated sensor from contact with the liquid, but allowed humid air to penetrate and create a controlled relative humidity (RH) level over the sensor. In both modules the temperature can be controlled from room temperature to 50° C. For this Example, all the QCMD measurements were carried out at room temperature.

Figure 1B:
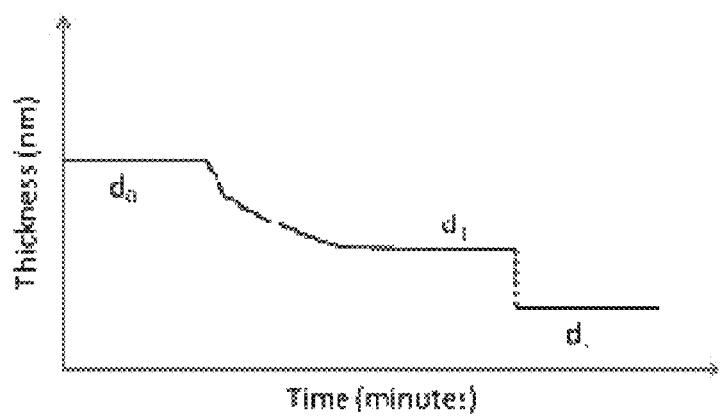

In the QCMD flow module test, the film thickness of the dry adhesive film was first measured using QCMD. Then water was passed through the chamber where an adhesive coated sensor was placed. The oscillating frequency change was recorded until equilibrium reached, which took approximately 1 hr. The modeling within the Q-Sense software allowed calculation of the film thickness and weight changes. After the QCMD run, the sensor with the remaining coating film was re-dried and the film thickness was measured again. Two typical curves shown in FIGS. 1A and 1B have been constructed based on the QCMD results, one for a relatively insoluble film such as Sample A and another for a soluble adhesive film such as Sample B.

The % insolubility and rewet ratio were calculated as follows:

$$\% \text{ Insolubility} = \frac{d2}{d0} \times 100$$

$$\text{Rewet Ratio} = \frac{d1}{d2}$$

Figure 2:
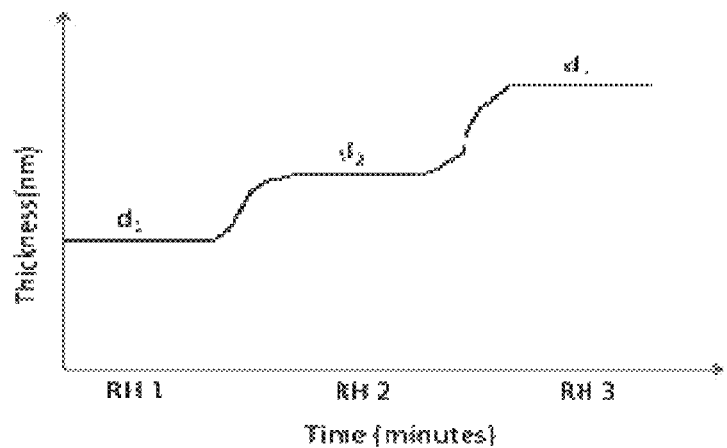
FIG. 2 graphically illustrates a film thickness profile calculated from the QCMD test with a humidity module.

In the humidity module test, a liquid with a salt solution was passed through the cell to generate the predetermined relative humidity level (e.g., RH1, RH2, RH3, etc.). A thickness change as shown in FIG. 2 was calculated using the Q-sense modeling software. A typical curve was observed for tested adhesive as the RH was changing.

The rewet ratio was calculated as follows:

$$\text{Rewet ratio } 1 = \frac{d2-d1}{d1} \times 100 \text{ for a change between } RH1 \text{ to } RH2$$

$$\text{Rewet ratio } 2 = \frac{d3-d1}{d1} \times 100 \text{ for a change between } RH1 \text{ to } RH3.$$

The humidity module rewet ratio is different from the flow module rewet ratio since one is measured in humid air and another in water, but both can be useful indicators of the creping adhesive performance.

A shear modulus corresponding to each RH level was also calculated using the Q-sense modeling software.

Peel Adhesion Test:

An adhesive film was cast on a hot metal plate using a wire-wound rod. The film was cured for a set time before a wet cotton strip was pressed into the film. After the strip and the film were dried for a set time, the peel force was measured in a 180° peel test under controlled temperature and peel speed. Two temperature conditions were used to simulate extreme curing conditions: (1) Low temperature (LT)—90° C. for 30 sec and (2) High temperature (HT)—110° C. for 5 min.

Figure 3A:
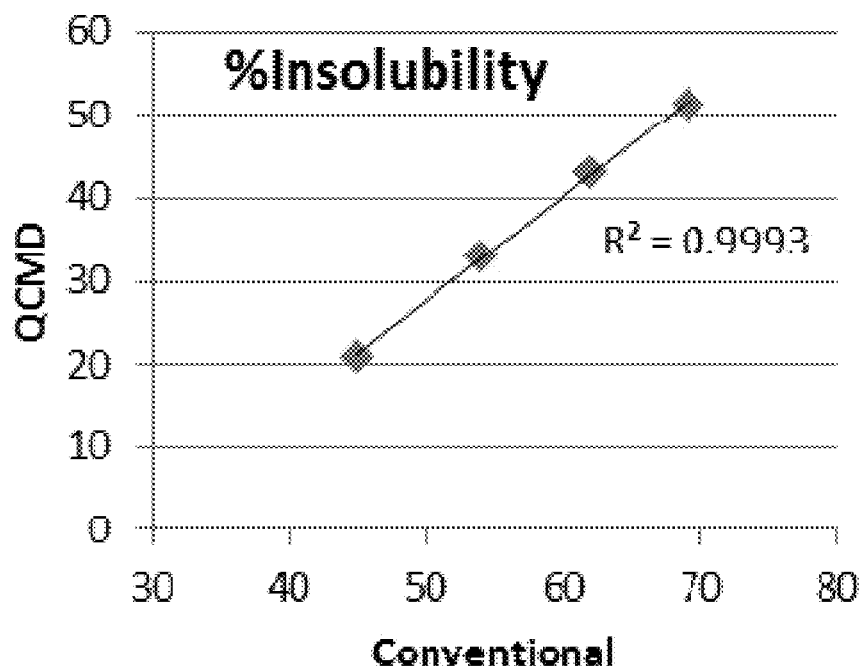
FIGS. 3A to 3C graphically illustrate correlations between the % insolubility, rewet ratio, and shear modulus, measured by conventional and QCMD methods.
Figure 3B:
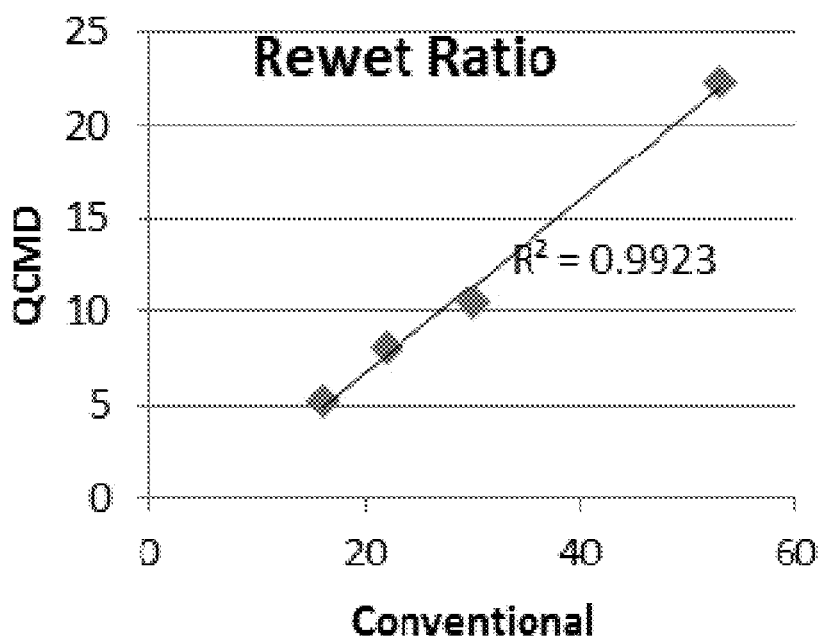
Figure 3C:
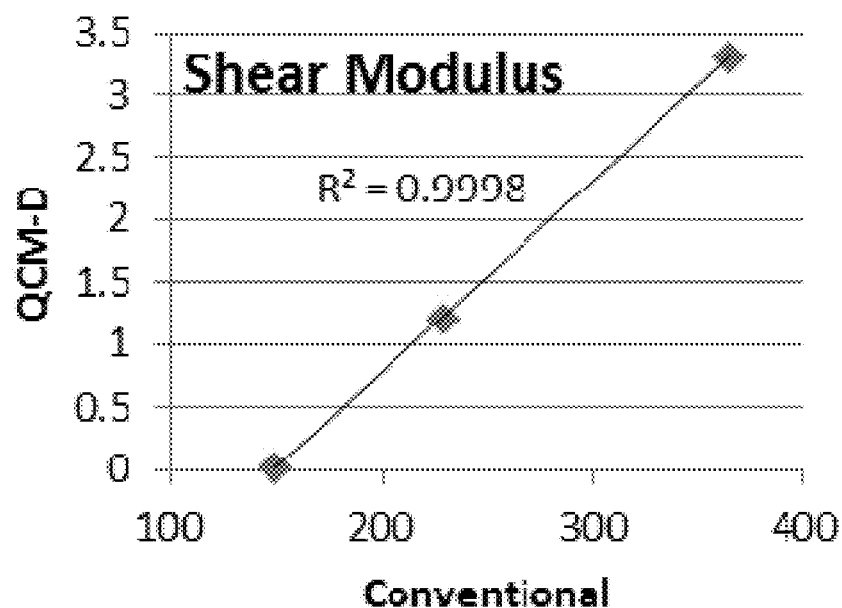
Figure 4A:
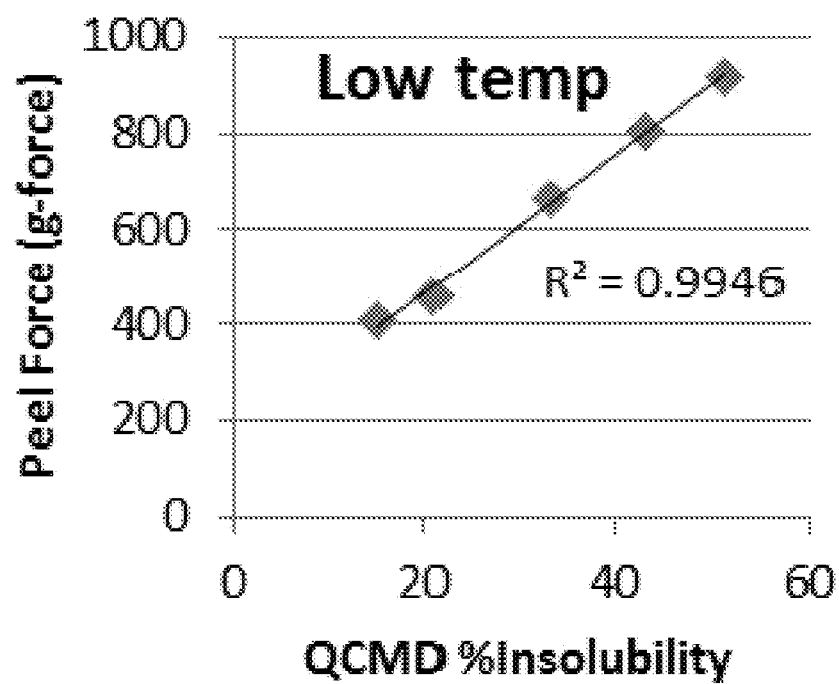
FIGS. 4A to 4F graphically illustrate correlations between adhesive characteristics measured by QCMD at peel adhesion at two extreme temperatures.
Figure 4B:
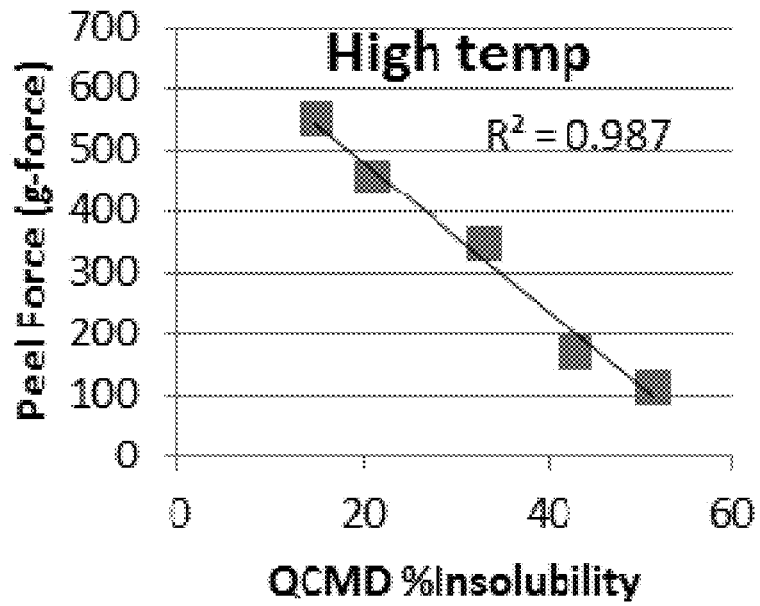
Figure 4C:
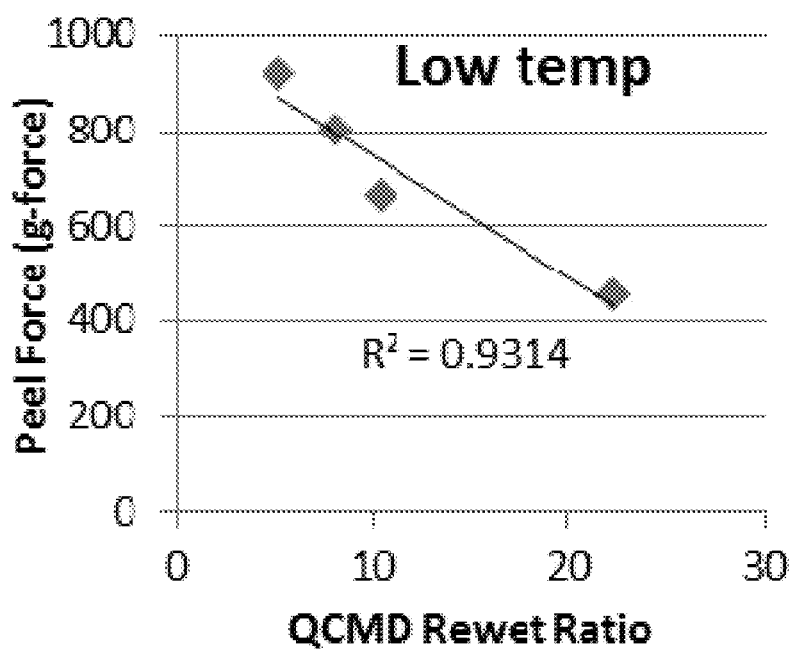
Figure 4D:
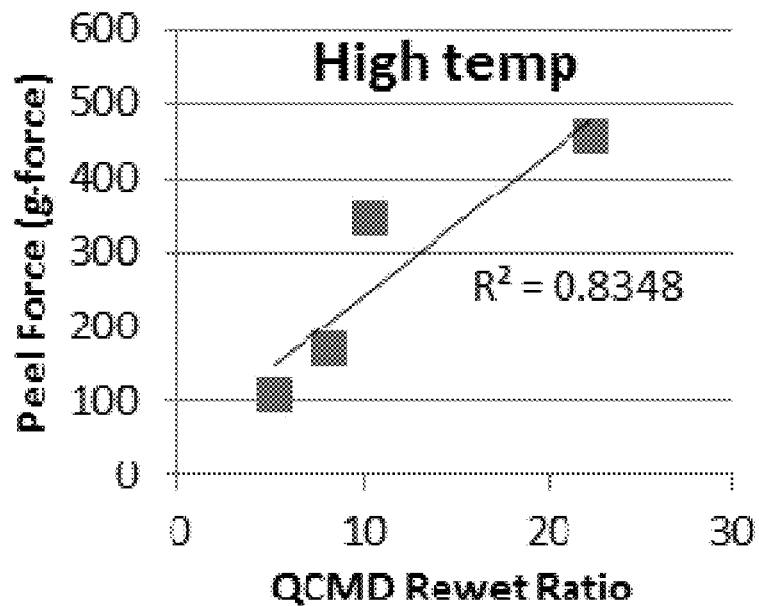
Figure 4E:
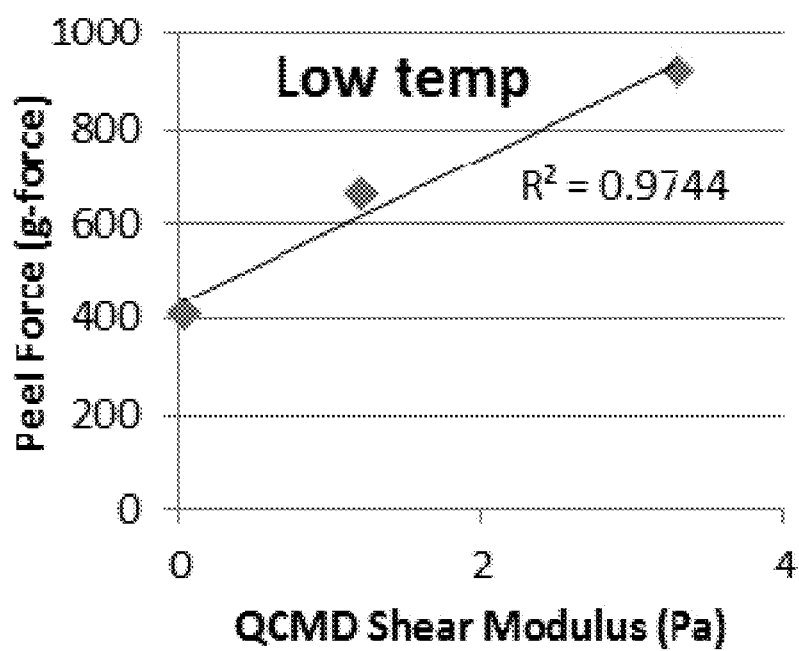
Figure 4F:
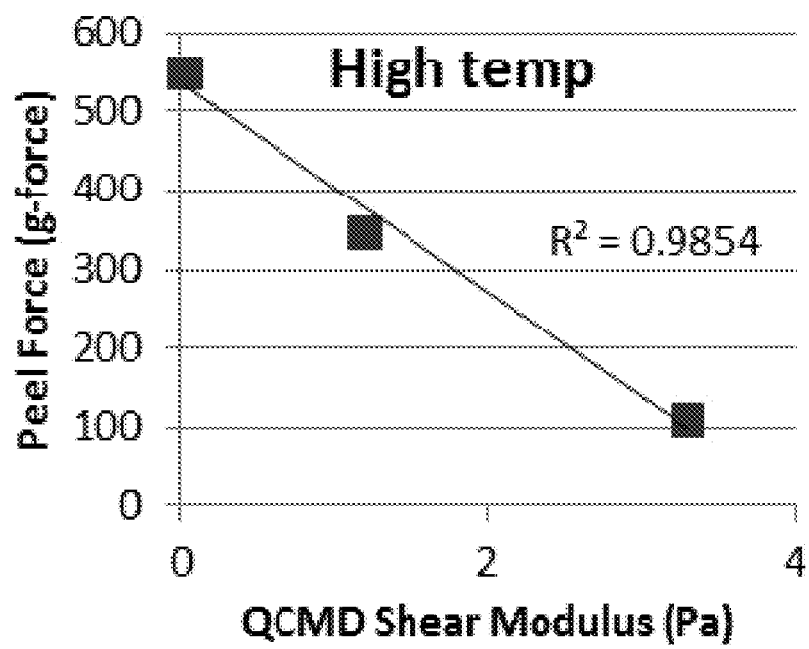

Crepe Adhesive Characteristics Measurements:

Table 1 summarizes characteristics of two commercial adhesives, Sample A and Sample B, and their blends measured using both conventional and QCMD methods. The results in FIGS. 3A to 3C show excellent linear correlations between % insolubility, rewet ratio, and shear modulus, measured by conventional and QCMD methods.

TABLE 1

Characteristics of creping adhesives measured by conventional and QCMD techniques.

| Sample A/ Sample B blends (dry basis ratio) | Conventional methods | | | QCMD methods | | |
|---|---|---|---|---|---|---|
| | % Insolubility | Rewet ratio | Shear Modulus (kPa) | % Insolubility | Rewet ratio (flow module) | Shear Modulus (Pa) (humidity module) |
| 100/0 | 69 | 16 | 365 | 51 | 5.2 | 3.3 |
| 75/25 | 62 | 22 | | 43 | 8.1 | |
| 50/50 | 54 | 30 | 230 | 33 | 10.4 | 1.2 |
| 25/75 | 45 | 53 | | 21 | 22.3 | |
| 0/100 | 0 | n/a* | 150 | 15 | 6.5 | 0.02 |

The data points for 100% Sample B were not used in correlations for % insolubility and rewet ratio because Sample B completely solubilizes in the conventional test; whereas in the QCMD test soluble adhesive films can still be fully characterized.

The data in Table 2 shows that the time required for QCMD measurements was significantly shorter than for conventional methods.

TABLE 2

Time required for measuring crepe adhesive characteristics using conventional and QCMD methods.

| Measured characteristics | Test Time for Conventional methods (hr) | Test Time for QCM-D methods (hr) |
|---|---|---|
| % Insolubility | 10 | 5 |
| Rewet ratio | 10 | 5 |
| Shear modulus | 10 | 3 |

Furthermore, QCMD data can be used to predict adhesion performance of creping adhesives. Table 3 summarizes the data for creping adhesive characteristics measured by QCMD method and corresponding peel adhesion data at two test temperatures. The two peel test temperatures exemplify extreme conditions on the Yankee dryer, which would require different film adhesive characteristics with regard to insolubility, rewet, and shear modulus.

TABLE 3

Film characteristics measured using QCMD and corresponding peel adhesion.

| Sample A/ Sample B blends (dry basis ratio) | QCMD methods | | | Peel Adhesion | |
|---|---|---|---|---|---|
| | % Insolubility | Rewet ratio | Shear Modulus (Pa) | Peel Force at low temperature (LT) (g-force) | Peel Force at high temperature (HT) (g-force) |
| 0 | 51 | 5.2 | 3.3 | 920 | 110 |
| 25 | 43 | 8.1 | | 805 | 170 |
| 50 | 33 | 10.4 | 1.2 | 665 | 345 |
| 75 | 21 | 22.3 | | 455 | 455 |
| 100 | | | 0.02 | 410 | 550 |

FIGS. 4A to 4F illustrate the correlation between peel force and the characteristics measured by QCMD. The QCMD methods predict that an adhesive producing a highly insoluble film with a low rewet ratio and high shear modulus (hard film) should provide high adhesion when the Yankee dryer temperature runs on a low side. This is consistent with practical observations that require a harder and less moisture sensitive coating to perform well under low temperature creping operations. In contrast, for the high temperature Yankee dryer, the QCMD method predicts that a more soluble, highly rewettable and soft film (low shear modulus) is preferred to provide high adhesion. Again, this is consistent with a desire for soft and rewetable coating for high temperature creping operations.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to the numerical value and what is being measured. In addition, the phrase "about 'x' to 'y'" includes "about 'x' to about 'y'".

It should be emphasized that the above-described embodiments of the present disclosure are merely possible examples of implementations, and are merely set forth for a clear understanding of the principles of this disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

We claim at least the following:

1. A method of measuring and modifying a characteristic of a creping adhesive film disposed on a dryer, comprising:
    disposing a creping adhesive film on a sensor substrate;
    measuring an oscillation frequency of the sensor substrate having the creping adhesive film disposed thereon using a Quartz Crystal Microbalance (QCM) technique, wherein the oscillation frequency is measured within conditions representing processing conditions of the creping adhesive film within the dryer;
    determining a characteristic of the creping adhesive film based at least in part on the measured oscillation frequency; and
    modifying the creping adhesive film based at least in part on determining the characteristic.

2. The method of claim 1, wherein the dryer comprises a Yankee Dryer.

3. The method of claim 1, further comprising measuring an oscillation frequency dissipation of the sensor substrate after a driving potential is removed from the sensor substrate.

4. The method of claim 1, further comprising:
    exposing the sensor substrate to a humid environment, wherein the creping adhesive film absorbs water from the humid environment; and
    measuring an oscillation frequency of the sensor substrate using the QCM technique.

5. The method of claim 3, further comprising measuring an oscillation frequency dissipation of the sensor substrate after the driving potential is removed from the sensor substrate.

6. The method of claim 1, further comprising:
    disposing a quantity of water onto the creping adhesive film, wherein the creping adhesive film absorbs the water; and
    measuring an oscillation frequency of the sensor substrate using the QCM technique.

7. The method of claim 1, further comprising measuring an oscillation frequency dissipation of the sensor substrate after a driving potential is removed from the sensor substrate.

8. The method of claim 1, wherein the characteristic is selected from the group consisting of: percent solubility, percent insolubility, rewet ratio, swelling ratio, film viscosity, film elasticity, film softness, film rigidity, shear modulus, and a combination thereof.

9. The method of claim 1, wherein measuring an oscillation frequency includes measuring at two or more frequencies that are applied to the sensor substrate.

10. The method of claim 9, further comprising measuring an oscillation frequency of the sensor substrate at two or more temperatures using the QCM technique.

11. The method of claim 10, wherein the creping adhesive film includes a component selected from the group consisting of: a release aid, a modifier, a plasticizer, a humectant, a phosphate, a creping additive, and a combination thereof.

12. The method of claim 10, wherein the creping adhesive film includes a component selected from the group consisting of: a mineral, a hemicellulose, a fiber, a fine, a fiber fragment, and a combination thereof.

13. The method of claim 10, wherein the creping adhesive film includes a component selected from a group consisting of: a softener, a debonder, a defoamer, a wet strength resin, a dry strength resin, a charge control agent, a retention aid, a biocide, a dye, and a combination thereof.

14. The method of claim 1, further comprising exposing the sensor substrate at a first temperature, wherein the first temperature is a temperature of about 10° C. to 100° C.

15. The method of claim 1, wherein the QCM technique includes Quartz Crystal Microbalance with Dissipation (QCMD).

16. A method of measuring and modifying a characteristic of a creping adhesive film disposed on a dryer, comprising:
    disposing a creping adhesive film on a sensor substrate;

measuring an oscillation frequency of the sensor substrate having the creping adhesive film disposed thereon using a Quartz Crystal Microbalance (QCM) technique;

measuring an oscillation frequency dissipation of the sensor substrate after a driving potential is removed from the sensor substrate;

exposing the sensor substrate to a humid environment, wherein the creping adhesive film absorbs water from the humid environment;

measuring an oscillation frequency of the sensor substrate using the QCM technique;

determining a characteristic of the creping adhesive film within the conditions of the dryer; and modifying the creping adhesive film based at least in part on determining the characteristic.

17. The method of claim 16, wherein the QCM technique includes Quartz Crystal Microbalance with Dissipation (QCMD).

18. The method of claim 16, wherein the characteristic is selected from the group consisting of: percent solubility, percent insolubility, rewet ratio, swelling ratio, film viscosity, film elasticity, film softness, film rigidity, shear modulus, and a combination thereof.

19. The method of claim 16, wherein the creping adhesive film is disposed on a Yankee dryer.

20. A method for modifying a creping adhesive film disposed on a Yankee dryer, comprising:

obtaining a sensor substrate having a creping adhesive film disposed thereon via a dip coating technique, wherein the creping adhesive film has a composition that is the same as a creping adhesive film disposed on a Yankee dryer;

measuring an oscillation frequency of the sensor substrate having the creping adhesive film disposed thereon using a Quartz Crystal Microbalance (QCM) technique;

determining a characteristic of the creping adhesive film, wherein the characteristic represents at least one processing condition of the creping adhesive film within the Yankee Dryer; and modifying a composition of the creping adhesive film disposed on the Yankee dryer based at least in part on the determination of the characteristic.

* * * * *